March 28, 1972 S. McGREDY Plant Pat. 3,091
ROSE PLANT
Filed Dec. 29, 1969
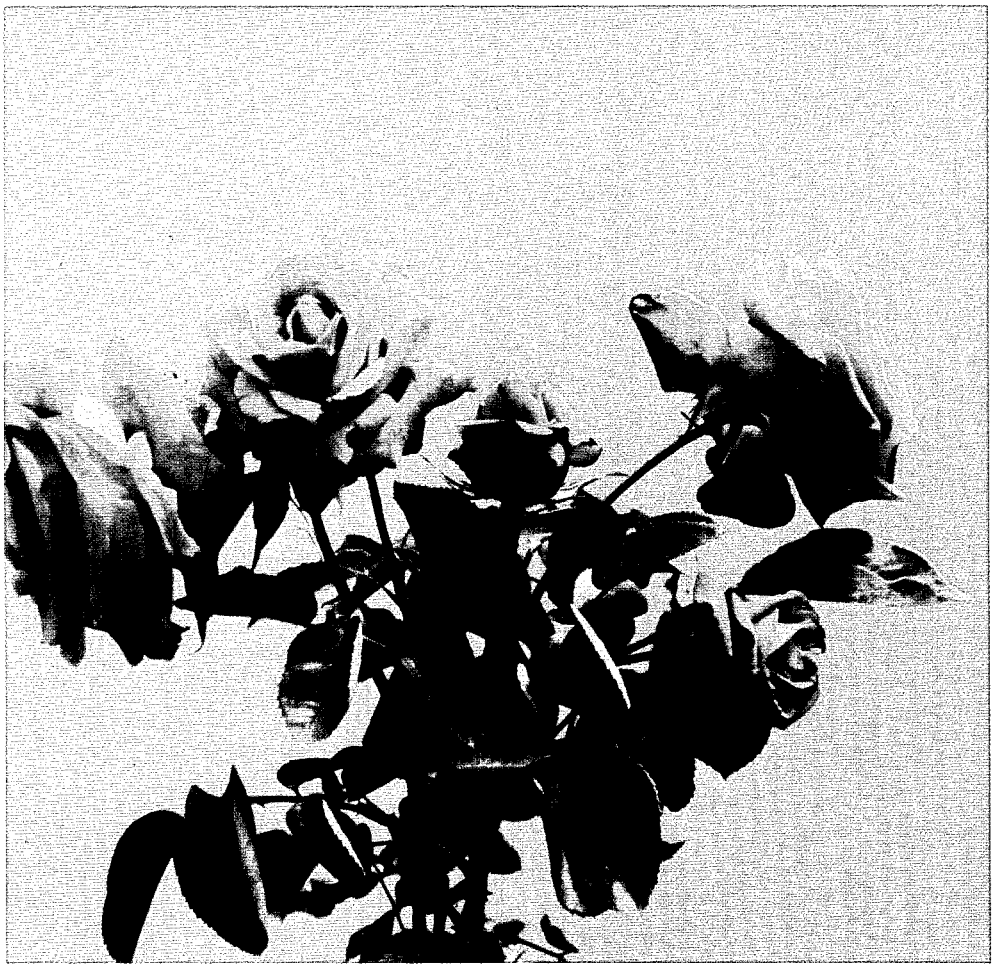

United States Patent Office

Plant Pat. 3,091
Patented Mar. 28, 1972

3,091
ROSE PLANT

Samuel McGredy, % McGredy & Son Ltd.,
Portadown, Northern Ireland

Filed Dec. 29, 1969, Ser. No. 889,006
Int. Cl. A01h *5/00*
U.S. Cl. Plt.—20 1 Claim The invention relates to a new and distinct variety of rose plant of the hybrid tea class, originated by me in 1958 as a consequence of a breeding program begun in 1958. The parentage of my new rose plant is as follows:

Karl Herbst × Ethel Sanday

The object of the cross was to combine the good flower form and color of Karl Herbst with the freedom of Ethel Sanday. These objectives were achieved along with other desirable improvements, as evidenced by the following unique combination of characteristics which are outstanding in the new variety and which distinguish it from its parents as well as from all other varieties of which I am aware. My new variety is primarily characterized by:

The flower is smaller than Karl Herbst with much clearer scarlet color, having a stronger neck and a more compact plant than most other red hybrid teas.

Asexual reproduction of my new variety by budding, through a series of propagations at Portadown, Northern Ireland, and Santo Rosa, California, shows that all characteristics of the variety come true to form through succeeding propagations. The accompanying photographs illustrate the primary characteristics of my new variety as nearly true as is reasonably possible to make them with presently available techniques. The color references cited are those of the Horticultural Colour Charts of the Royal Horticultural Society.

The following botanical description is based upon observation of field and container grown plants.

The plant habit is erect with ascending canes. Secondary branching is moderate to heavy. The canes are graceful with varying diameters averaging 5–6 mm. They are Willow Green (HCC 000862/1) in color, darkening with age. On the average at maturity, the overall plant height ranges between 45–75 cm. with a width of 40 cm. or more. The armature is moderate with about 2–4 major thorns per internode. The thorns are small with a basal length of about 0.8 cm. and an extension of 0.6 cm. The internode length is normally about 4–5 cm.

The foliage is abundant and odd-pinnate having 3–5 leaflets, with 5 being usual. The overall leaf length is around 10 cm. (including the petiole). The leaflets are ovate and tend to be apiculate, serrate, leathery, semi-glossy, sessile, and have a slightly convoluted surface. The apical leaflet is about 4 cm. long by 3 cm. wide on the average. The rachis is ribbed on the upper surface and has an occasional thorn on the lower surface. When the leaf is immature the rachis and petiole have numerous, scattered prickles that do not persist to maturity. The leaflet color is Fern Green (HCC 0862) variously anastomosed with Leek Green (HCC 000858) on the upper surface and Sage Green (HCC 000861/1) on the lower surface. The new leaflets are very heavily shot with Erythrite Red (HCC 027/1) on the lower surface and some Oxblood Red (HCC 00823) shot over the Fern Green (0862) upper surface. The leaflets are doubly serrate and turn upward becoming flattened with age. The petiole is ribbed and stipulate. The stipules are apically appendaged, ciliate, 2–3 mm. wide and are adnate about ½ the length of the petiole. The petiole length is about 3 cm. The petiole and rachis are Pod Green (HCC 061) on the lower surface.

The inflorescence is solitary. The bud is pointed, becoming urceolate, and is about 2 cm. long by 1.5 cm. wide at anthesis. The bud color is predominantly Dahlia Purple (HCC 931) with the lower ⅓ of the petal being Tyrian Purple (HCC 727). The bud opens to a full, high-centered flower with a diameter of 9.5 cm. and a depth of 3.5 cm. The fragrance is moderate and spicy. The petals number is about 30 with about 7–16 petaloids. The petals are obovate, crisp, velvety, imbricated, with rolled or slightly wavy margins. Petal size is about 4.5–4.75 cm. long by 4.25 cm. wide. The outer petals are Cherry (HCC 722) anastamosed with Tyrian Purple (HCC 727) and Dahlia Purple (HCC 931) on the inner surface and are Rose Red (HCC 724) on the outer surface. The inner petals are Rose Bengal (HCC 25) with Dahlia Purple (HCC 931) on the margins on the inner surface and China Rose (HCC 024 and 024/1) on the outer surface of the petals.

The peduncle is Pod Green (HCC 061) when shaded or Oxblood Red (HCC 00823) when sunburned and has scattered, minute prickles. The sepals are truncate, lanceolate, moderately to ornately appendaged, cilicate, pubescent within and glabrous without. Sepal color is Pod Green (HCC 061) shot with Oxblood Red (HCC 00823). The sepals reflex at maturity and persist. The hypanthium is glabrous without, hairy within, funnelform, becoming urceolate at anthesis. The hypanthium color is Pod Green (HCC 061). The disk is prominent, glabrous, and light green. The stamens number about 128 with yellowish filaments that turn pinkish near the anther. The anther cells are pinkish with light yellow dehiscing surfaces. Upon dehiscence; the cells become black with golden dehiscing surfaces. The pistils number about 115 with white, hairy styles that turn pink near the light yellow stigmas.

The plant is mildew and disease resistant and shows little fading in the sun.

Having thus disclosed my invention, I claim:

1. A new and distinct variety of rose plant of the hybrid tea class substantially as herein shown and described primarily characterized by:

the flower is smaller than Karl Herbst with much clearer scarlet color, having a stronger neck and a more compact plant than most other red hybrid teas.

No references cited.

ROBERT E. BAGWILL, Primary Examiner